United States Patent [19]

Panzone et al.

[11] Patent Number: 5,594,102
[45] Date of Patent: Jan. 14, 1997

[54] CHEMICAL PROCESS FOR PREPARING ANTIBIOTIC L 17932 (DEGLUCOTEICOPLANIN) AND ITS SALT

[75] Inventors: Giambattista Panzone, Cornaredo; Anacleto Gianantonio, Milan, both of Italy

[73] Assignee: Gruppo Lepetit S.p.A, Gerenzano, Italy

[21] Appl. No.: 453,114

[22] Filed: May 30, 1995

Related U.S. Application Data

[63] Continuation of Ser. No. 323,162, Oct. 13, 1994, abandoned, which is a continuation of Ser. No. 126,670, Sep. 24, 1993, abandoned, which is a continuation of Ser. No. 987,103, Dec. 7, 1992, abandoned, which is a continuation of Ser. No. 827,553, Jan. 28, 1992, abandoned, which is a continuation of Ser. No. 453,443, Dec. 20, 1989, abandoned.

[30] Foreign Application Priority Data

Dec. 27, 1988 [EP] European Pat. Off. ............. 88121707

[51] Int. Cl.$^6$ ..................................... C07K 7/64
[52] U.S. Cl. ........................ 530/317; 530/322; 530/345
[58] Field of Search ............................ 530/317, 322, 530/45

[56] References Cited

U.S. PATENT DOCUMENTS

| | | | |
|---|---|---|---|
| 4,239,751 | 12/1980 | Coronelli et al. | 424/118 |
| 4,604,239 | 8/1986 | Michel et al. | 530/317 |
| 4,629,781 | 12/1986 | Strazzolini et al. | 530/317 |
| 4,645,827 | 2/1987 | Malabarba et al. | 530/322 |
| 4,698,418 | 10/1987 | Malabarba et al. | 530/317 |
| 4,725,668 | 2/1988 | Strazzolini et al. | 530/317 |
| 4,868,171 | 9/1989 | Selva et al. | 424/118 |
| 4,882,419 | 11/1989 | Malabarba et al. | 530/317 |

FOREIGN PATENT DOCUMENTS

| | | |
|---|---|---|
| 0146053 | 6/1985 | European Pat. Off. . |
| 228015 | 7/1987 | European Pat. Off. . |
| 255299 | 2/1988 | European Pat. Off. . |
| 0301247 | 6/1988 | European Pat. Off. . |
| 0306645 | 6/1988 | European Pat. Off. . |

OTHER PUBLICATIONS

Journal of Antibiotics vol. 39, No. 10, pp. 1430–1442, 1986.
Zanol, M., Cometti, A., Borghi, A., Lancini, G. C., "Isolation and Structure Determination of Minor Components of Teicompanin", (1988), Chromatographia, vol. 26, pp. 234–236.
McGahren et al., The Journal of Antibiotics, vol. 36, No. 12, pp. 1671–1682 (1983).
Bardone et al., The Journal of Antibiotics, vol. 31, No. 3, pp. 170–177 (1978).
Ellestad et al., The Journal of Antibiotics, vol. 36, No. 12 pp. 1683–1690 (1983).
Harris et al., J. Am. Chem. Soc. vol. 105, pp. 6915–6927 (1983).

*Primary Examiner*—Howard E. Schain
*Attorney, Agent, or Firm*—Ruth E. Homan

[57] ABSTRACT

The present invention is directed to a chemical process for preparing antibiotic L 17392 (deglucoteicoplanin) and its salts with bases and acids by submitting a teicoplanin compound or a teicoplanin-like compound to controlled strong acid hydrolysis in the presence of an organic aprotic solvent, and a purification thereof.

20 Claims, No Drawings

CHEMICAL PROCESS FOR PREPARING ANTIBIOTIC L 17932 (DEGLUCOTEICOPLANIN) AND ITS SALT

This is a continuation of application Ser. No. 08/323,162, filed Oct. 13, 1994, now abandoned which is a continuation of application Ser. No. 08/126,670, filed Sep. 24, 1993, now abandoned, which is a continuation of application Ser. No. 07/987,103, filed Dec. 7, 1992, now abandoned, which is a continuation of application Ser. No. 07/827,553, filed Jan. 28, 1992, now abandoned, which is a continuation of application Ser. No. 07/453,443, filed Dec. 20, 1989, now abandoned, which is herein incorporated by reference.

The present invention is directed to the obtainment of an antibiotic substance arbitrarily designated as antibiotic L 17392 or deglucoteicoplanin and its salts with bases and acids.

The antibiotic substances possess antimicrobial activity mainly against gram-positive bacteria (e.g. Staphylococcus and Streptococcus strains). This antibiotic is obtained by chemical transformation of a teicoplanin compound or teicoplanin-like compound.

Teicoplanin is the international non-proprietary name (INN) of the antibiotic substance formerly named teichomycin which is obtained by cultivating the strains *Actinoplanes teichomyceticus* nov. sp. ATCC 31121 in a culture medium containing assimilable sources of carbon, nitrogen and inorganic salts (see U.S. Pat. No. 4,239,751).

According to the procedure described in the above cited patent, an antibiotic complex (identified as teichomycin) containing factors $A_1$, $A_2$ and $A_3$ is recovered from the fermentation broth by extraction with a suitable water insoluble organic solvent and precipitation from the organic solvent according to common procedures.

Factor $A_2$, which is the preponderant factor of the isolated antibiotic complex, is then separated from the other factors by means of column chromatography on SEPHADEX. Factor $A_1$ and factor $A_3$ are present only in minor amounts. British Patent No. 2121401 discloses that antibiotic factor $A_2$, in turn, actually is a mixture of five closely related co-produced main components.

From a fermentation and purification (for instance, through column chromatography) operations a teicoplanin product is currently obtained which essentially consists of factor $A_2$ accompanied by minor amounts of factor $A_3$.

Recent studies shows that teicoplanin factor $A_2$ and its individual components may be represented by the following formula I

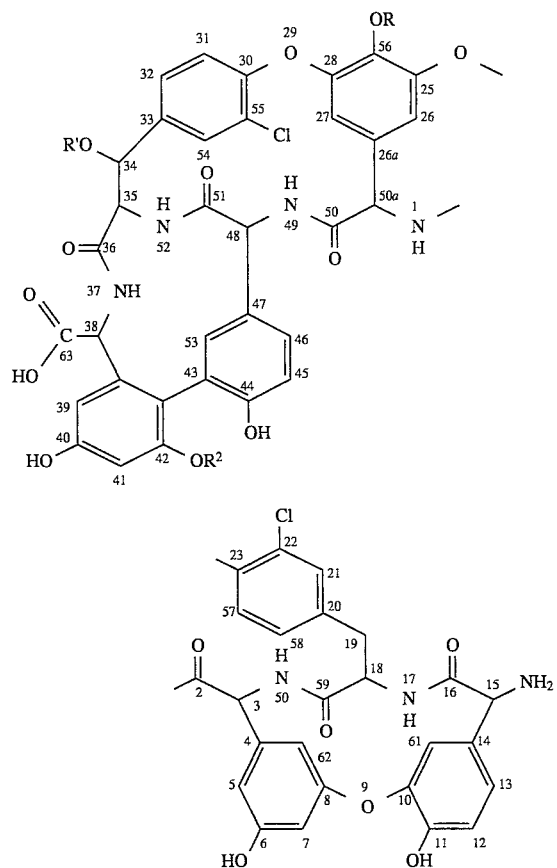

wherein

R is a N-[($C_9$–$C_{12}$)aliphatic acyl]-D-glucosamine rest, $R^1$ is a N-acetyl-D-glucosamine rest, and $R^2$ is a D-mannose rest.

All sugar moieties identified above are linked to the core/molecule through O-glycosidic bonds. A substance having the same structural formula is disclosed in EPA Publication No. 0090578 and is named antibiotic A 41030 factor B. This substance is obtained by means of a microbiological process Which involves the fermentation of the strain *Streptomyces virginiae* NRRL 12525 or *Streptomyces virginiae* NRRL 15156 in a suitable medium, the isolation, purification and separation into its components of antibiotic A 41030, an antibiotic complex of at least seven factors, antibiotic A 41030 factor B, included.

In the European Patents No. 119574 and 119575 have been described partial hydrolysis products of teicoplanin factor $A_2$ wherein one or two sugar moieties are split off. These products are respectively named antibiotic L 17054 and L 17046. The products are obtained by submitting teicoplanin factor $A_2$ to some specific acid hydrolysis conditions. For L 17054 the hydrolysis is preferably carried out by using 0.5N hydrochloric acid at a temperature between 70° C. and 90° C. for 15 to 90 minutes. For L 17046, the hydrolysis is preferably carried out by using hydrochloric acid at a concentration from 1N to 3N at a temperature between 70° C. and 90° C. for 30 to 60 minutes.

Antibiotic L 17054 may be represented by the formula I above, whereby R is replaced by hydrogen, $R^1$ is a N-acetyl-D-glucosamine rest and $R^2$ is a D-mannose rest. Antibiotic L 17046 may be represented by the formula I above wherein R and $R^2$ are both replaced by hydrogen and $R^1$ is a N-acetyl-D-glucosamine rest. European Patent Application Publication No. 301247 describes the de-mannosyl teicoplanin derivatives, i.e. compounds of the formula I above wherein R and $R^1$ are as above and $R^2$ is hydrogen. In this specification and claims, with the term "teicoplanin compound" it is indicated a substance selected from the teicoplanin complex obtained by fermentation of *Actinoplanes teichomyceticus* ATCC 31121 followed by purification operations according to U.S. Pat. No. 4,239,751, any further purified preparation thereof, teicoplanin factor $A_2$, teicoplanin factor $A_3$, each of the main components of teicoplanin factor $A_2$.

De-mannosylated teicoplanin derivatives can be obtained in good yield by microbiological transformation of a substrate selected from teicoplanin complex, any mixture of the single components and a single component thereof with cultures of *Nocardia orientalis* NRRL 2450 or *Streptomyces candidus* NRRL 3218, their natural mutants of variants exhibiting the same property of splitting the glycosidic bond with the D-mannose moiety in the teicoplanin molecule, the washed mycelium or a cell-free preparation thereof.

The first above mentioned strain is also referred to in the recent literature as *Streptomyces orientalis* NRRL 2450 (see: S. K. Chung et al., The Journal of Antibiotics 39, No. 5, page 652–659, 1986).

Samples of said strains A/156 and S/802 respectively have been redeposited on June 10, 1987 at the ATCC (American Type Culture Collection, 12301 Parklawn Drive, Rockville, Md. 20852 U.S.A.) under the conditions established by the Budapest Treaty on the International Recognition of the Deposit of Microorganisms for the Purposes of Patent Procedure where have been assigned the following ATCC numbers respectively 53630 and 53629.

When the teicoplanin complex or a mixture of its single components is used as a substrate for the microbiological transformation, the resulting product is a mixture of five de-mannosyl derivatives of teicoplanin. Said mixtures can be used as such for the uses described herein or can be optionally separated into the five individual components by means of known techniques such as, for instance, reverse-phase partition, ion exchange chromatography of preparative HPLC (see for reference U.S. Pat. No. 4,542,018).

The de-mannosyl teicoplanin derivatives are prepared by submitting a substrate selected from teicoplanin complex, any mixture of the single components and a single component thereof which can be represented by formula I above wherein the aliphatic acyl group of the beta-D-2-deoxy-2-aminoglucopyranosyl moiety is:

TA2-1): N-(Z-4-decenoyl)-beta-D-2-deoxy-2-amino-glucopyranosyl;

TA2-2): N-(8-methyl-nonanoyl)-beta-D-2-deoxy-2-amino-glucopyranosyl;

TA2-3): N-decanoyl-beta-D-2-deoxy-2-amino-glucopyranosyl;

TA2-4): N-(8-methyl-decanoyl)-beta-D-2-deoxy-2-amino-glucopyranosyl;

TA2-5): N-(9-methyl-decanoyl)-beta-D-2-deoxy-2-amino-glucopyranosyl;

$R_1$ is N-acetyl-beta-D-2-deoxy-2-amino-glucopyranosyl;
$R_2$ is alpha-D-mannopyranosyl to a microbiological transformation with a microorganism selected from strain *Nocardia orientalis* NRRL 2450, *Streptomyces candidus* NRRL 3218, the natural variants and mutants thereof exhibiting the same property of splitting the glycosidic bond with the D-mannose moiety in the teicoplanin molecule, the washed mycelium and a cell-free preparation thereof.

According to a preferred embodiment, the selected starting material either in pure form or in the form of any crude preparation thereof, including harvested fermentation broth from *Actinoplanes teichomyceticus* nov. sp. ATCC 31121, is contacted with a growing culture of one of the above strains under fermentation conditions.

The above mentioned strains are cultivated under usual submerged aerobic conditions in a medium containing assimilable sources of carbon, nitrogen and inorganic salts.

Generally, the starting material mentioned above can be added to a culture of *Nocardia orientalis* NRRL 2450 or *Streptomyces candidus* NRRL 3218, at a time varying from 18 hours from the inoculation time to the time at which the culture has reached its maximum growth, however, addition after 24–72 hours from inoculation is, at least in some instances, preferred.

The reaction time, i.e. the time of exposure of the starting material to the microbial culture before recovering the final product, may vary between 48 and 140 hours, depending on the specific conditions employed. Anyway, since the reaction can be monitored as known in the art, for instance by following the decrease of the starting material and/or the increase of the final product by HPLC, the skilled man is capable of readily determine when the reaction is to be considered as complete and the recovery procedure can be started.

Instead of employing a growing culture of *Nocardia orientalis* NRRL 2450 or *Streptomyces candidus* NRRL 3218, one may employ a culture of any mutant or variant thereof which is still capable of splitting the glycosidic bond between the phenolic moiety and the mannose portion of the above mentioned starting material to give the corresponding de-mannosylated compounds.

Moreover, de-mannosylated teicoplanin compounds can be prepared according to this method by using a mycelium of the above identified de-mannosylating microorganism culture, washed in an isotonic saline solution, conveniently NaCl, in order not to disrupt said aqueous solution of mycelium.

After having washed the mycelium, it is conveniently resuspended in a physiologically acceptable medium. The washed mycelium procedure can be used in order to increase the amounts of teicoplanin compounds to be reacted while maintaining optimal yields. It is also possible to carry out a cell-free preparation obtained by disrupting the cells, e.g. by sonication.

The recovery of the de-mannosyl teicoplanin antibiotic substances from the reaction medium is then conducted according to known per se techniques which include extraction with solvents, precipitation by adding non-solvents or by changing the pH of the solution, partition chromatography, reverse-phase partition chromatography, ion-exchange chromatography, affinity chromatography and the like.

A preferred procedure includes an affinity chromatography on immobilized D-Alanyl-D-Alanine followed by separation at different pH.

Immobilized D-Alanyl-D-Alanine matrices suitable for the present recovery process are disclosed in European Patent Application Publication No. 122969. The preferred matrix in this recovery process is D-Alanyl-D-Alanine coupled with a controlled pore cross-linked polydextrane.

The reaction medium can be subjected to the affinity chromatography directly after filtration or after a preliminary purification procedure. This latter procedure includes making the whole medium basic, preferably between pH 8.5 and 11 and then filtering in the presence of a filter aid, if convenient.

The clear filtrate is then adjusted to a pH value between 7 and 8 and then subjected to an affinity chromatography on immobilized D-Alanyl-D-Alanine, either in column or batchwise.

While the binding of the substance to the affinity matrix is preferably made at a pH of about 7.0–8.0, its elution is performed at more basic pH values (preferably between 9.0 and 10.5) by means of an aqueous base. This aqueous base may be ammonia, a volatile amine, an alkali or alkali metal hydroxide or a basic buffered solution optionally in the presence of a polar organic solvent such as a polar water-miscible solvent.

Representative examples of polar water-miscible solvents are: water-soluble alcohols, (such as methanol, ethanol, isopropanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

After removing the impurities by rinsing the column with aqueous buffer pH 4–9, optionally containing salts, (e.g. ammonium formate) urea and/or water-miscible solvents, the de-mannosyl teicoplanin antibiotic substance is eluted with the above eluting mixture. The eluate is analyzed by HPLC and the fractions containing the desired material are pooled together.

This eluate is adjusted to pH 7.0–7.5 with an organic or mineral acid.

The eluate is then submitted to concentration and desalting procedures.

A convenient desalting procedure includes applying the antibiotic containing aqueous solution to a silanised silica gel column, washing with distilled water and eluting with a mixture of a polar water-miscible solvent as defined above and water.

Alternatively, the aqueous solution of the de-mannosylated teicoplanin derivative(s) is submitted to simultaneous concentration/desaltion procedures by ultrafiltration through a ultrafiltration membrane with a nominal molecular weight limit (NMWL) or 1000 dalton or less.

The solution obtained from the above procedure is then lyophilized and the recovered material is submitted to further purification.

In some cases, in particular, for large scale preparations, it is preferred to carry out said purification in two steps. The first one is carried out according to a reverse phase chromatography general procedure already described in U.S. Pat. No. 4,542,018 for the separation of the individual factors of teicoplanin complex. According to a specific embodiment of said procedure, the de-mannosyl teicoplanin derivative(s) product obtained from lyophilization is dissolved in an ammonium formate/acetonitrile mixture and adjusted a pH 7.5 with sodium hydroxide and the obtained solution is passed through a silanised silica gel column and then the column is eluted with a linear gradient of acetonitrile in ammonium formate solution. The eluate is monitored by HPLC and the fractions containing the desired material(s) are pooled together and evaporated under reduced pressure yielding the solid material desired. This procedure is also useful for the separation of the single de-mannosyl derivatives of teicoplanin complex when this latter or a mixture of its single components is used as the starting material instead of the individual components.

The first purification step may be avoided when the starting material utilized for the microbiological transformation is sufficiently pure and essentially consists of an individual components of teicoplanin complex.

The second purification step involves a semi-preparative HPLC on a silanised chemically modified preparative HPLC column by using two mixtures of acetonitrile/ammonium formate in different ratios as mobile phases and maintaining a linear gradient of acetonitrile in ammonium formate. The eluted fractions are monitored by HPLC analysis and those containing the desired product are pooled together, the organic solvent is evaporated under reduced pressure and then the aqueous solution is submitted to simultaneous concentration/desaltion by ultrafiltration as described above. The solution resulting from ultrafiltration is then lyophilized yielding the desired pure product. "teicoplanin compounds" includes teicoplanin RS-3 (compound A) and RS-4 (compound B) described in European Patent Application Publication No. 306645. These compounds may be represented through the formula I above wherein $R^1$ and $R^2$ are as above and the aliphatic acyl moiety of the radical R are respectively 10-methyl-undecanoyl, dodecanoyl, 6-methyl-octanoyl and nonanoyl. With the term "teicoplanin-like compound" it is hereby indicated any compound having the same basic structure formula I as above wherein R is hydrogen or a N-[($C_9$-$C_{12}$)aliphatic acyl]-D-glucosamine rest, $R^1$ is hydrogen or a N-acetyl-D-glucosamine rest, $R^2$ is hydrogen or a D-mannose rest with the proviso that R, $R^i$ and $R^2$ cannot be simultaneously hydrogen, and a mixture of two or more of any of the above substances and/or compounds in any proportion.

Raw extracts, rich in RS-1 and RS-2 were obtained from the mother liquors of the preparation of several batches of teicoplanin. RS-3 and RS-4 were obtained by fermentation from a mutant strain of *A. teichomiceticus*, producing substantial amounts of these two components.

Preparative HPLC

RS-1 and RS-2: About 500 mg. of crude extract were charged in each run on the Jobin Yvon chromatograph, equipped with a column (50 cm×2 cm I.D.), packed with 7 um RP-18(Merk) and eluted with a mixture of 0.02M monobasic sodium phosphate/acetonitrile 73/27. After evaporation of the acetonitrile under vacuum, the extract was passed through a column of RP-8(home made) and eluted first with water, to eliminate salt, and then with water/acetonitrile 30/70. The partially enriched mixture of RS-1 and RS-2 thus obtained was then separated by preparative HPLC, using the HP 1084 Chromatograph equipped with a 7 um RP-18 column (Merk, 25cm×1 cm I.D.) and the same phosphate/acetonitrile eluent used in the first step. After a second desalination step, carried out as described above, and the elimination of acetonitrile, the aqueous fractions containing RS-1 and RS-2 were lyophilized.

European Patent Application Publication No. 146053 describes a chemical process for preparing antibiotic L 17392 (deglucoteicoplanin i.e. the compound of formula I wherein R, $R^1$ and $R^2$ are simultaneously hydrogen atoms) by submitting a teicoplanin compound or a teicoplanin like compound to controlled strong acid hydrolysis characterized in that an organic protic solvent selected from aliphatic acids, alpha halogenated aliphatic acids, aliphatic and cycloaliphatic alkanols, and phenyl substituted alkanols, is used.

According to the disclosure of European Patent Application Publication No. 146053 it is also necessary to employ a strong acid compatible with the solvent such as a strong mineral acid or a strong organic acid, and carry out the reaction at a temperature between about 20° C. and about 100° C.

In the "Journal of Antibiotics" Vol. 39, No. 10 pp. 1430–1442 October 1986 the preparation and the NMR characteristics of deglucoteicoplanin are described. In said reference different methods for preparing deglucoteicoplanin, by hydrolysis in an organic polar solvent of a teicoplanin and teicoplanine like compounds are reported.

According to an object of this invention it has been found that antibiotic L 17392 (deglucoteicoplanin) and its salts with bases and acids may be obtained by submitting to controlled strong acidic hydrolysis conditions a teicoplanin compound or a teicoplanin-like compound in a polar aprotic organic solvent selected from N,N-dimethylformamide (DMF), hexamethyl phosphoramide (HMPA), 1,3-dimethyl 3,4,5,6-tetrahydro-2 (IH) pyrimidone (DMPV) and, dimethyl sulfoxide (DMSO) or mixture thereof. The "controlled strong acidic hydrolysis conditions" which are suitable for the process of this invention are those reaction conditions whereby it is provided sufficient acid strength to provoke the removal of all sugar moieties of teicoplanin compounds and/or teicoplanin-like compounds without simultaneously provoking other undesired modifications or alteration of the chemical structure and chiral centers of the substrate.

It is known that removal of all sugar moieties from a complex molecular structure such as that of glycopeptide antibiotics always presents considerable difficulties since mild acid hydrolysis conditions usually afford only partial removal of sugars moieties while strong acid hydrolysis conditions promote partial degradation of the substrate and/or changes in the stereochemical configuration of chiral centers. For instance, for avoparcin, a known glycopeptide antibiotic, the true aglycone was never isolated.

The following scientific literature support the above considerations: G. A. Ellestad et al., J. of Antibiotics, 36, 1683 (1983); C. M. Harris et al., J. Am. Chem. Soc. 105, 6915 (1983); W. J. McGahren et al., J. of Antibiotics, 36, 1671 (1983). M. R. Bardone et al., (J. of Antibiotics, 31, 170 (1978)) describes hydrolytic treatments of teichomycin factor $A_2$ both with aqueous 2N $H_2SO_4$ and with aqueous 6N HCl at 100° C.

It has been found that with the process of the present invention the molar yield of deglucoteicoplanin is remarkably high (about 65%). The yields of deglucoteicoplanin of the processes of the prior-art depend on the particular combination solvent/reactant used. For example by using trifluoroacetic acid as solvent and HCl as acid medium it is possible to have yields comparable to those of the present invention, while by employing $H_2SO_4$ the yields of the prior-art processes are lower than 10%. Alternative methods disclosed in the prior-art which apparently give very high yields (about 90% of the crude product), have the drawbacks of being necessarily carried out in a heterogenous medium (suspension of the starting material in a liquid polar solvent, bubbling the mineral acid) and actually afford a crude product which has a very low grade of purity. For instance in Example 4 of European Patent Application Publication No. 146053 starting from a suspension of ten grams of teicoplanin complex in benzyl alcohol, using HCl as mineral acid at a temperature of 60° C., 9.2 g of crude deglucoteicoplanin are obtained.

However after chromatographic purification only 1.5 g of substantially pure product are recovered.

Furthermore, in view of a scaling up of the process it is important to carry out the reaction in a homogeneous medium in order to have a better reproducibility of the quality of the product, such as a better homogenization of the granulometry and less analytical problems during the reaction course.

With the process of the invention it is possible to have good yields of deglucoteicoplanin having a good grade of purity and to carry out the reaction in a homogeneous medium.

According to the object of this invention the "controlled strong acid hydrolysis conditions" outlined above are provided by properly selecting the solvent, the type of acid, its concentration, and the temperature of the reaction. In fact, it is hereby provided a process for transforming a teicoplanin compound or a teicoplanin-like compound into deglucoteicoplanin and its salts with bases and acids, characterized in that a substance selected from teicoplanin complex, any further purified preparation thereof, teicoplanin factor $A_2$, teicoplanin factor $A_3$, each of the main components of teicoplanin factor $A_2$, a compound of formula I above wherein R is hydrogen, or a N-[($C_9$–$C_{12}$)aliphatic acyl]-D-glucosamine rest, $R^1$ is hydrogen or a N-acetyl-D-glucosamine rest, $R^2$ is hydrogen or a D-mannose rest with the proviso that R, $R^1$ and $R^2$ cannot be simultaneously hydrogen, and a mixture of two or more of any of the above substances in any proportion, is submitted to controlled strong acid hydrolysis conditions in a homogenous medium by employing an organic aprotic solvent selected from N,N-dimethylformamide (DMF), hexamethyl phosphoramide (HMPA), 1,3-dimethyl-3,4,5,6-tetrahydro-2(1H) pyrimidone (DMPV) and dimethylsulfoxide (DMSO) a mixture thereof, and a strong acid compatible with the solvent selected from a strong mineral acid and a strong organic acid.

The organic aprotic solvent has to be liquid at the reaction temperature and has to be capable of completely solubilizing the teicoplanin starting material.

The organic aprotic solvent which is particularly preferred is dimethylsulfoxide.

The strong acid which is needed to provide the controlled strong acid hydrolysis conditions of the process of the invention can be a strong mineral acid or a strong organic acid.

Among the strong mineral acids hydrochloric acid, hydrobromic acid, concentrated sulfuric acid and concentrated phosphoric acid are preferred. Among the strong organic acids the alpha-halogenated lower aliphatic acids, the alkanesulfonic acids, the polyfluoroalkanesulfonic acids, the cycloalkanesulfonic acid and the arylsulfonic acids are preferred, with the following being the most preferred ones: trifluoroacetic acid, trichloroacetic acid, methanesulfonic acid, ethanesulfonic acid, trifluoromethanesulfonic acid, benzenesulfonic acid, cyclohexanesulfonic acid, camphorsulfonic acid, alpha and beta naphthalene sulfonic acid and p-toluenesulfonic acid. The concentrated acids are preferably employed in large excess (by weight) on the starting teicoplanin or teicoplanin-like compound. Sulfuric acid and phosphoric acid are usually employed at the highest concentration commercially available. In particular, 95% to 98% (w/w) sulfuric acid and 85% to 98% (w/w) orthophosphoric acid yield satisfactory results. However, the process can be carried out also by any strong mineral acid at lower concentration, such as for instance 30% to 80%. Among the organic acids, 98% (w/w) methanesulfonic acid and 98% (w/w) trifluoroacetic acid are preferably employed according to a preferred embodiment of this invention.

The content of water in the reaction mixture must be sufficient to meet the stoichiometric requirement of the hydrolysis reaction. On the other side, it is desirable to keep the amount of water in the reaction mixture as low as possible to prevent unwanted side reactions such as degradation of the reaction product, or rearrangement and/or isomerization of the chiral centers of the substrate.

For meeting the stoichiometric requirements of the reaction and, at the same time, keeping the rate and the process operability at an industrially valuable level, the hydrolysis process is usually carried out in the presence of an amount of water which is ranging from about 1% to about 20% by weight of the starting teicoplanin or teicoplanin-like compound.

The sufficient water amount may be supplied together with the acid or it may be originally contained in the starting substrate. When essentially anhydrous starting material, solvent and acid are employed, the desired amount of water may be directly added to the solvent or to the reaction mixture.

When a mineral acid is used, the total concentration of the acid in the reaction mixture depends on the particular acid used but usually ranges between 1% (w/v) and 10% (w/v).

For example when $H_2SO_4$ is used the concentration may range between 2% and 7% (w/v), more preferably between 3% and 5%, while when HCl is employed it is preferred to use a lower concentration, for example comprised between 1% and 3% (w/v).

As a general illustration of the controlled strong acid hydrolysis process, the teicoplanin or teicoplanin-like compound is stirred in a molar excess of the selected solvent at room temperature and then the proper acid is added. The reaction mixture is then reacted and maintained with stirring at the desired temperature for a period of time enough to achieve satisfactory yields of deglucoteicoplanin. The reaction time is usually determined by monitoring the reaction through analytical tests. For the purpose of giving a general indication without limiting the scope of this invention, the reaction time may generally range between 0.25 and 20 hours, depending on the starting material, the solvent(s), the strong acid, its concentration and the temperature of the reaction. The temperature of the reaction is properly selected for each reaction system, taking into accounts the following factors: the starting materials, the type of the organic aprotic solvent, the type and the concentration of the acid, and their mutual proportions. Lower reaction temperature usually requires a longer reaction time for obtaining satisfactory conversion yields. In general the controlled strong acid hydrolysis process is carried out at a temperature between about 50° C. and about 120° C.

A preferred temperature range is between 60° C. and 100° C. with the range between 75° C. and 85° C. being the most preferred one.

At the end the reaction mixture is poured into demineralized water under stirring and the pH is adjusted to about 7.0 with a basic aqueous solution such as for example 10% acqueous NaOH. The reaction mixture is then filtered. The solid obtained by filtration is washed with a small amount of water and dried at 50° C. under vacuum for two hours.

In a preferred embodiment of the invention DMSO is used as solvent in the presence of 98% (w/w) $H_2SO_4$ at a temperature of about 85° C. The concentration of the sulfonic acid in the total volume of the reaction mixture is generally comprensive between 3% and 5%. Generally, after hydrolysis the solid crude product has a purity of about 30–35%.

In a further aspect of the invention, the crude deglucoteicoplanin obtained as described above can be easily purified by simple acid-base precipitation from a DMSO/water mixture, thus avoiding any further purification step.

Infact it is known that by using the hydrolysis methods of the prior-art it is necessary to purify the deglucoteicoplanin by column chromatography for example, by use of a reverse phase column chromatography employing silanized silica gel as adsorbent and hydrophilic mixtures as eluent.

Obviously, any purification procedure known in the art can be used for purifying the crude deglucoteicoplanin obtained through the process of the invention, although a purification procedure which comprises a chromatographic method has the disadvantage of requiring elution times and amounts of solvent which are not adequated to the scaling up of the process.

Therefore a further object of the invention is a process for purifying deglucoteicoplanin which comprises dissolving said deglucoteicoplanin in a suitable solvent mixture containing DMSO/$H_2O$ at a pH value lower than about 4 or higher than about 10, reprecipitating the product adjusting the pH of the solution between 6 and 8, preferably at 7, and filtering the resulting pure solid.

The pH value of the solution is brought to a value lower than 4 or higher than 10 in order to solubilize deglucoteicoplanin as an acid or base salt in a reasonable small volume of the solution thus lowering the loss of the final product when it is precipitated.

For example addition of strong mineral acids such as HCl, HBr or $H_2SO_4$ can be preferably used in order to obtain the acid salt form.

An alkali hydroxide such as NaOH is preferably used when is desired to dissolve deglucoteicoplanin in a base salt form.

The DMSO/$H_2O$ solvent mixture has to show a good dissolution power toward the deglucoteicoplanin starting material.

Usually the DMSO concentration in the DMSO/water mixture ranges between 30% and 70% (v/v) preferably between 40% and 60%. With 10 to 20 weight proportions of mixture of this latter range it is generally possible to dissolve one weight proportion of crude deglucoteicoplanin at the above mentioned acid or basic pH value.

In a preferred embodiment of this particular aspect of the invention a DMSO/water mixture containing 40–60% DMSO/water in the presence of 10% aqueous hydrochloric acid sufficient to bring the pH value at about 4 is used to dissolve the crude deglucoteicoplanin (30–35% HPLC titre).

The deglucoteicoplanin obtained by precipitation from the solution through adjustement of the pH at a neutral value comprised between 6 and 8, preferably at 7 is a product in form of free base, which does not require any further purification step.

In case that the crude deglucoteicoplanin has a purity grade lower than 30% it may be necessary to repeat the solution/precipitation step.

A final double sludge of the solid, first with acetone and then with demineralized water can be also introduced into this procedure in order to eliminate the residual DMSO. The thus obtained product is substantially pure deglucoteicoplanin showing satisfactory physico-chemical and biological characteristics for use in the applications described below.

Substantially pure deglucoteicoplanin has an HPLC titre greater than 95% (percent peak areas, at the 254 nm U.V. wavelength), a water and solvent content from 10% to 15% by weight and an inorganic residue lower than 0.5% by weight.

The physico-chemical characteristics of the deglucoteicoplanin as obtained with the process of the invention are reported in the European Patent Application Publication No. 146053 already cited.

Deglucoteicoplanin obtained according to this process can be optionally transformed into the corresponding salts with bases and acids through commonly known procedures.

Deglucoteicoplanin and its pharmaceutically acceptable salts with bases and acids can effectively be employed as the active ingredient of antimicrobial preparations used in human and veterinary medicine for the prevention and treatment of infectious diseases caused by pathogenic bacteria which are susceptible to said active ingredients. In such treatments, these compounds may be employed as such or also in the form of mixtures in any proportion. The data concerning in vitro and in vivo activity of deglucoteicoplanin, as well as the way of formulating it are disclosed in European Patent Application Publication No. 146053.

However, deglucoteicoplanin can be used as the starting material for the preparation of valuable semisinthetic teicoplanin derivatives such as those described in European Patent Application Publication No. 218099 and International Patent Application Publication No. WO 88/06600.

The following examples illustrate the manner in which the invention can be practiced, but, as such, should not be construed as limiting its overall scope.

EXAMPLE 1

Preparation of Deglucoteicoplanin from Teicoplanin Complex 4.5 g of Teicoplanin complex sodium salt (i.e. sodium salt of the antibiotic complex containing teichomycin factors $A_1$, $A_2$ and $A_3$ and obtained by fermentation of strain ATCC 31121 according to U.S. Pat. No. 4,239,751) were suspended in about 42 ml of DMSO at room temperature (20° C.) and 1 ml of 95% $H_2SO_4$ (corresponding to 4.1% w/v in the whole reaction mixture).

The mixture was stirred until the teicoplanin was dissolved and then heated at 85° C. for 20 hours. The hydrolysis was monitored via HPLC every hour injecting a 30 microg. sample of the solution diluted 50 times.

After cooling at room temperature the reaction mixture was poured out under stirring in 70 ml of demineralized water and the pH adjusted to 7.00 with 10% of NaOH. The obtained precipitate was collected by filtration, washed with a small amount of water on the filter and then dried at 50° C. under vacuum to obtain 2.74 g (52% titre) with a molar yield of 61% crude deglucoteicoplanin.

EXAMPLES 2 TO 7

By substantially following the procedure of Example 1 but using the reaction conditions reported in Table I below deglucoteicoplanin was prepared:

(HPLC assay 82%) were dissolved while stirring, at room temperature (22°–24° C.) in a mixture of 2.5 l of acetone and 300 ml of 30% aq. HCl.

Stirring was continued for 48 hours, then the solution was cooled in an ice water bath at 3° C. and slowly neutralized with 20% aq. NaOH, keeping the solution temperature under 10° C. Then the acetone was completely distilled under reduced pressure (bath temp. 40° C.) and the residual water suspension, 2 l filtered at pH=7.

The crude solid pseudoaglycone (33.2 g), was dissolved again in 1.2 l of distilled water at pH 9.5 (aq. NaOH), the resulting solution was clarified by filtration, and the pseudoaglycone precipitated again bringing the pH to 6.5 with 10% aq. HCl. After filtration the white wet solid was sludged with 200 ml of fresh acetone, filtered again, and dried for 20 hours under vacuum at room temperature.

23.5 g of the-title compound was obtained (HPLC titre 70%) with a yield of 54%. The purification of the crude product was carried out according to known procedures (as described in European Patent Application Publication No. 146 053) yielding 12.8 g of 90% pure title compound.

B) Preparation of Deglucoteicoplanin

By substantially following the procedure of Example 1 but using the pseudoaglycone above prepared (5 g) instead of teicoplanin complex and by employing 40 ml of DMSO as solvent, 95% $H_2SO_4$ (1 ml, 4.1 w/v) as mineral acid, maintaining the reaction temperature at 100° C. (for 20 hours) 3,1 g (61% of molar yield) of the crude deglucoteicoplanin were prepared.

EXAMPLE 9

Purification of the Crude Deglucoteicoplanin 1052 g of crude light brown solid deglucoteicoplanin prepared as in Example 1 were dissolved under stirring in a mixture of DMSO (7.5 l), demineralized water, (7.5 l) and 300 ml of 20% aqueous hydrochloric acid (300 ml). When the solution was complete further 4.5 l of water were added under stirring and the pH of the solution was brought to 7 using 350 ml of 20% aqueous NaOH. The suspension was then cooled to 5° C. for 2 hours and the solid deglucoteicoplanin filtered and dried at room temperature in the air. 525 g of the product (HPLC assay 68%, DMSO content 17%) was obtained with yield of 65%. The mother liquors, 19 l, contained 14 g of deglucoteicoplanin (2.5%).

TABLE I

| Example No. | Amount of DMSO (ml) | Type and amount of acid (ml) | | % of acid w/v | Temperature °C. | Yield % |
| --- | --- | --- | --- | --- | --- | --- |
| 1 | 40 | 80% $H_2SO_4$ | 1 | 3.0 | 85 | 62 |
| 3 | 40 | 37% HCl | 2 | 2.0 | 85 | 62 |
| 4 | 40 | 37% HCl | 1 | 1.7 | 85 | 61 |
| 5 | 42 | 25% HCl | 2 | 1.2 | 85 | 62 |
| 6 | 42 | 95% $H_2SO_4$ | 1 | 4.1 | 95 | 63 |
| 7 | 42 | 95% $H_2SO_4$ | 1 | 4.1 | 85 | 61 |

EXAMPLE 8

A) Preparation of Antibiotic L 17046 (Pseudoaglycone)

In a 3 l four neck round bottom flask equipped with a mechanical stirrer and a thermometer, 50 g of teicoplanin A second portion of 1000 g of starting material was hydrolyzed and purified following the same procedure reported above. 522.5 g of deglucoteicoplanin, assay 67.5%, was obtained with a 65.3% yield. The two purified deglucoteicoplanin samples (525 plus 522.5 g) were mixed together and then suspended under vigorous stirring in 15 l of acetone. Stirring was continued for 60 minutes then the solid was recovered by filtration and dried. 960 g of product was obtained. (HPLC assay: TD 71%, $H_2O$ 14,6%, solvents: DMSO 2.5%, acetone 9%).

In order to eliminate the residual solvents, 920 g of the solid deglucoteicoplanin were suspended again in demineralized water (8.5 l) and stirred for further 4 hours. After filtering and drying under vacuum at 30° C., 805 g of 80% pure deglucoteicoplanin was obtained. The results are summarized in Table II below.

TABLE II

| PURIFICATIONS STEPS | SOLID DEGLUCOTEICOPLANIN | | | | | | | MOTHER LIQUORS | | | |
|---|---|---|---|---|---|---|---|---|---|---|---|
| | g crude TD | HPLC % assay | g Pure TD | Yield % | HPLC % Distribution Areas | | | Pure TD | HPLC % Distribution Areas | | |
| | | | | | TD | TC | Other | g(Y %) | TD | TC | Other |
| First portion Hydrolysis and Precipitation | 525 | 68 | 357 | 65 | 94 | 2 | 4 | 14 (2.5) | 37 | 42 | 21 |
| Second portion Hydrolysis and Precipitation | 522 | 67.5 | 353 | 65.3 | 94 | 2 | 4 | — | — | | |
| Acetone Sludges | 960 | 71 | 681 | 63 | 94 | 3 | 3 | 0.5 | 26 | — | 74 |
| Water | 805 | 80 | 644 | 60 | 95 | 1 | 4 | 3.5 (0.7) | 84 | 2.5 | 13.5 |

EXPERIMENTAL PART

HPLC analysis were performed with a HEWLETT PACKARD mod. 1082 B apparatus equipped with a UV (254 nm) detector and a C. ERBA RP 18,5 um, 150×4 mm prepacked column.

The mobile phase were:
A) 0.025 M aqueous $NaH_2PO_4/CH_3CN$ 95:5 (v/v)
B) 0.025 M aqueous $NaH_2PO_4/CH_3CN$ 30:70 (v/v)

The chromatograms were obtained by a linear gradient elution from 8% of B in A to 75% of B in A in 45 min at a flow rate of 1.5 ml/min.

The reactions Were monitored by HPLC injecting at established times 30 microl. of the solution properly diluted with an acetonitrile/water mixture 2:8.

We claim:

1. A process for preparing pure deglucoteicoplanin or a salt thereof with bases and acids comprising;

1) a hydrolysis of a compound of Formula I

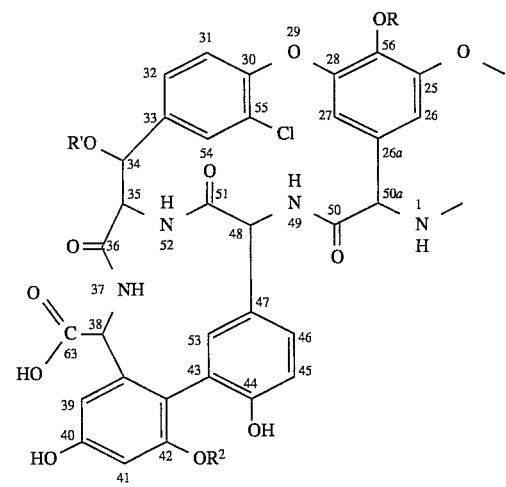

-continued

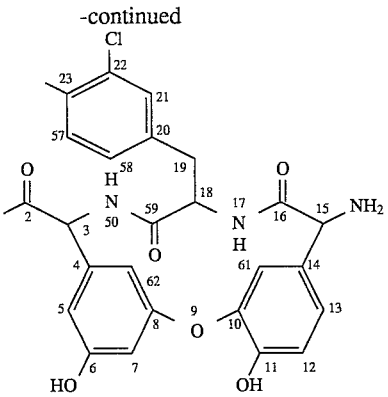

wherein

R is hydrogen or a N-[($C_9$–$C_{12}$)aliphatic acyl]-D-glucosamine;

R1 is hydrogen, or a N-acetyl-D-glucosamine;

R2 is hydrogen or d-manose;

with the proviso that R, $R_1$, and $R_2$ cannot be simultaneously hydrogen or a mixture of two or more of any of the above substances; to yield a deglucoteicoplanin crude product wherein the hydrolysis is a controlled acid hydrolysis in a homogeneous media which employs;

a) a reaction temperature between about 50° C. and 120° C.

b) an organic aprotic solvent, which is a liquid at the reaction temperature and which is selected from the group consisting of N,N dimethylformamide (DMF), hexamethylphospoamide (HMPA), 1.3-dimethyl-3, 4,5,6-tetrahydro-2(1H)pyrimidine (DMPU), and dimethylsulfoxide (DMSO) or mixtures thereof, c) water, d) a strong mineral acid or organic acid which is compatible with the organic aprotic solvent selected, 2) isolation of the crude product; and 3) purification of the deglucoteicoplanin crude product.

2. A process as in claim 1 wherein the organic aprotic solvent is dimethylsulfoxide.

3. A process as in claim 1 wherein the mineral acid is selected from hydrochloric acid, hydrobromic acid, sulfuric acid and phosphoric acid.

4. A process as in claim 1 wherein the mineral acid is sulfuric acid.

5. A process as in claim 1 further characterized in that the reaction temperature is between 60° C. and 100° C.

6. A process as in claim 1 further characterized in that reaction temperature is between 75° C. and 85° C.

7. A process as in claim 1 further characterized in that the concentration of the acid in the whole reaction mixture ranges between 1% w/v and 10% w/v.

8. A process as in claim 4 wherein the concentration of sulfuric acid ranges between 2% and 7% (w/v).

9. A process for purifying deglucoteicoplanin which comprises dissolving said deglucoteicoplanin in a solvent mixture containing DMSO/$H_2O$ at a suitable pH, reprecipitating the product adjusting the pH of the solution at substantially neutral value and filtering the resulting pure solid.

10. A process as in claim 9 wherein the concentration of DMSO in the DMSO/water mixture ranges between 30% and 70% (v:v).

11. A process as in claim 10 wherein the concentration of DMSO in the DMSO/water mixture ranges between 40% and 60% (v:v).

12. A process as in claim 9 further characterized in that the deglucoteicoplanin is dissolved in a solvent mixture containing DMSO/water at a pH brought to about 4 by addition of a strong mineral acid.

13. A process as in claim 12 wherein the strong mineral acid is selected from hydrochloric acid, hydrobromic acid and sulfuric acid.

14. A process as in claim 9 further characterized in that the deglucoteicoplanin is dissolved in a solvent mixture containing DMSO/water at pH brough to about 10 by addition of an alkali hydroxyde.

15. A process as in claim 14 wherein the alkali hydroxyde is aqueous NaOH.

16. A process as in claim 12 wherein the solid was precipitated at a pH comprised between 6 and 8.

17. A process as in claim 16 wherein the solid is precipitated at pH 7.

18. A process as in claim 9 which is further characterized in that a double sludge of the solid, first with acetone and then with demineralized water is carried out after the reprecipitation of the deglucoteicoplanin.

19. A process according to claim 1 further characterized in that the reaction mixture contains water in an amount from 1% to 20% by weight relative to the teicoplanin starting material.

20. The process according to claim 1 in which the purification employs;
   a) solubilization of the crude product in a mixture of dimethyl sulfoxide and water,
   b) adjustment of solution pH; and
   c) a precipitation of the deglucoteicoplanin from the solution.

* * * * *